United States Patent
Takeuchi

(10) Patent No.: US 12,313,711 B2
(45) Date of Patent: May 27, 2025

(54) MEDICAL IMAGE DIAGNOSIS APPARATUS AND PICTURE PROJECTION APPARATUS

(71) Applicant: CANON MEDICAL SYSTEMS CORPORATION, Otawara (JP)

(72) Inventor: Daiki Takeuchi, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 119 days.

(21) Appl. No.: 18/186,247

(22) Filed: Mar. 20, 2023

(65) Prior Publication Data

US 2023/0305086 A1    Sep. 28, 2023

(30) Foreign Application Priority Data

Mar. 25, 2022 (JP) .................................. 2022-050678

(51) Int. Cl.
*G01R 33/28* (2006.01)
*A61B 5/00* (2006.01)
*A61B 5/055* (2006.01)
*G06T 7/70* (2017.01)

(52) U.S. Cl.
CPC ............ *G01R 33/283* (2013.01); *A61B 5/055* (2013.01); *A61B 5/704* (2013.01); *G06T 7/70* (2017.01); *G06T 2207/30004* (2013.01); *G06T 2207/30196* (2013.01)

(58) Field of Classification Search
CPC ......... G01R 33/283; A61B 6/46; A61B 6/461; A61B 6/462; A61B 5/055
See application file for complete search history.

(56) References Cited

U.S. PATENT DOCUMENTS

| 2016/0015330 | A1* | 1/2016 | Jo ......................... A61B 5/7435 600/415 |
| 2016/0018503 | A1* | 1/2016 | Lee ..................... G01R 33/283 324/309 |
| 2017/0119320 | A1* | 5/2017 | Ueda ....................... A61B 5/11 |
| 2017/0322271 | A1* | 11/2017 | Gulaka ................. A61B 6/462 |
| 2019/0038246 | A1* | 2/2019 | Hotta ..................... G02B 3/08 |

FOREIGN PATENT DOCUMENTS

JP    2020-195841 A    12/2020

* cited by examiner

*Primary Examiner* — Carolyn A Pehlke
(74) *Attorney, Agent, or Firm* — Oblon, McClelland, Maier & Neustadt, L.L.P.

(57) ABSTRACT

A medical image diagnosis apparatus according to an embodiment includes movable member which moves in a bore along the central axis of the bore formed in a gantry provided with a medical imaging mechanism concerning imaging a subject, couchtop which inserts into the bore, screen provided for the member and having a picture from a projector projected thereon, first frame connected to the member and positioned on the projector side for the screen, a second frame supporting a reflection board and being movable along the first frame, and processing circuitry which estimates a posture of the examined subject based on one of the position of the reflection board concerning the screen and the orientation of the head of the examined subject, determines a rotation amount of the picture on the basis of the posture, and controls the projector so as to rotate the picture according to the rotation amount.

4 Claims, 10 Drawing Sheets

MEDICAL IMAGE DIAGNOSIS APPARATUS AND PICTURE PROJECTION APPARATUS

CROSS-REFERENCE TO RELATED APPLICATIONS

This application is based upon and claims the benefit of priority from Japanese Patent Application No. 2022-050678, filed on Mar. 25, 2022, the entire contents of which are incorporated herein by reference.

FIELD

Embodiments described herein relate generally to a medical image diagnosis apparatus and a picture projection apparatus.

BACKGROUND

Magnetic resonance imaging apparatuses have a gantry provided with an imaging mechanism using a magnet or the like. The gantry has formed therein a bore having a substantially hollow shape. Magnetic Resonance (MR) imaging is performed while a patient is inserted in the bore. Although some gantries have been developed so as to have a relatively large bore diameter, not a few patients feel stressed by MR examinations because of MR imaging periods that can last for a long time, noise while the gantry is driven, and oppressed feelings and entrapped feelings inside the bore.

To reduce the oppressed feelings and entrapped feelings inside the bore, an apparatus has been proposed by which a picture is projected onto a screen from a projector, so that the picture can be viewed with a mirror. However, with this apparatus, because the projection direction of the picture is fixed, and the mirror is arranged in accordance with the direction, the patient is able to view the picture only in a supine posture.

DETAILED DESCRIPTION

Figure 1:
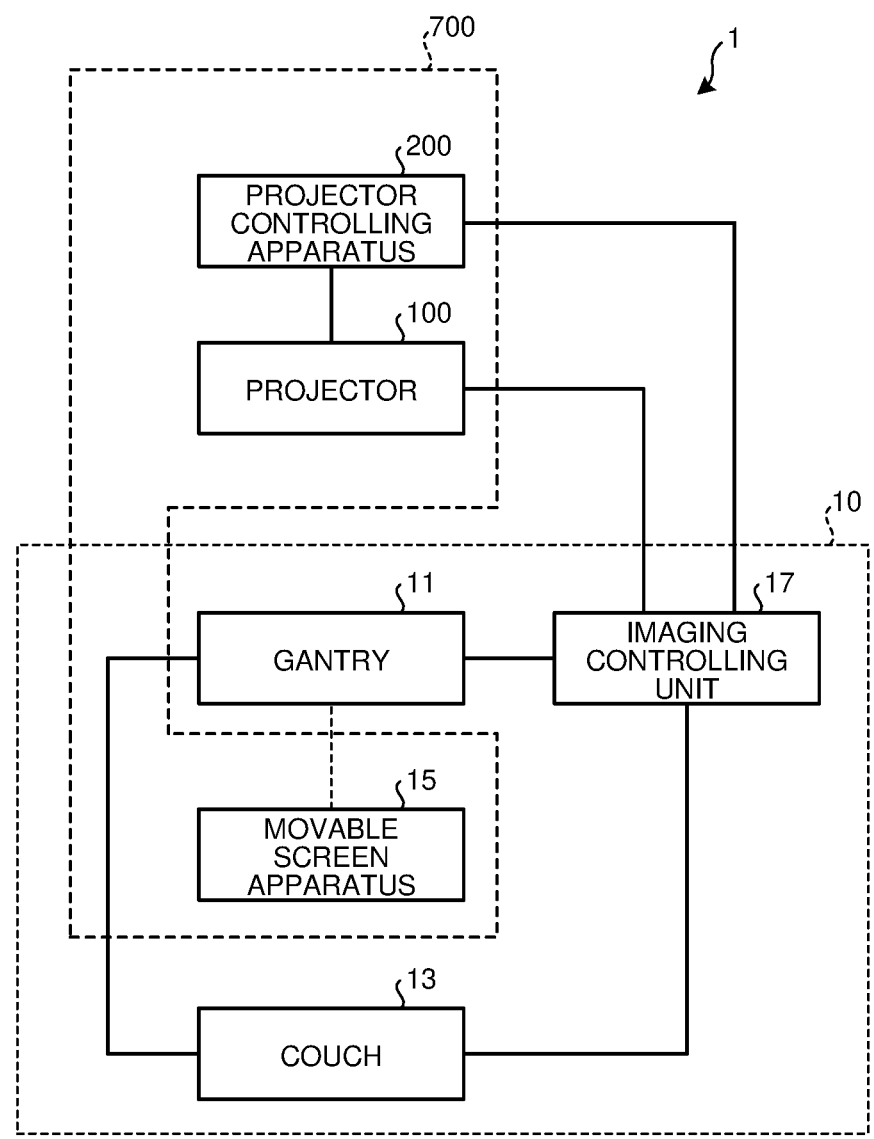
FIG. 1 is a diagram illustrating an exemplary configuration of a medical image diagnosis system including a medical image diagnosis apparatus according to an embodiment.

A medical image diagnosis apparatus according to an embodiment includes a movable member, a couchtop, a screen, a first frame, a second frame, and processing circuitry. The movable member is movable in a bore along the central axis of the bore, the bore being formed in a gantry provided with a medical imaging mechanism related to imaging an examined subject. The couchtop is configured to be insertable into the bore. The screen is provided for the movable member and is configured to have a picture from a projector projected thereon. The first frame is connected to the movable member and is positioned on the projector side relative to the screen. The second frame is configured to support a reflection board and is movable along the first frame. The processing circuitry is configured: to estimate a posture of the examined subject on the basis of one of the position of the reflection board with respect to the screen and the orientation of the head of the examined subject; to determine a rotation amount of the picture on the basis of the posture; and to control the projector so as to rotate the picture according to the rotation amount.

Exemplary embodiments of a medical image diagnosis apparatus of the present disclosure will be explained below, with reference to the accompanying drawings. In the following description, some of the constituent elements having substantially the same functions and configurations will be referred to by using the same reference characters, and duplicate explanations will be provided if necessary.

Embodiments

FIG. 1 is a diagram illustrating a configuration of a medical image diagnosis system 1 including a medical image diagnosis apparatus 10 according to an embodiment of the present disclosure. As illustrated in FIG. 1, the medical image diagnosis system 1 includes the medical image diagnosis apparatus 10, a projector 100, and a projector controlling apparatus 200 that are communicably connected to one another in a wired or wireless manner. The medical image diagnosis apparatus 10 includes a gantry 11, a couch 13, a movable screen apparatus 15, and an imaging controlling unit 17. For example, the gantry 11, the couch 13, and the movable screen apparatus 15 are installed in an examination room, whereas the imaging controlling unit 17 is installed in a control room adjacent to the examination room. The gantry 11 is provided with a mechanism for realizing medical imaging processes. The gantry 11 has formed therein a bore having a hollow shape. To the front of the gantry 11, the couch 13 is installed. The couch 13 is configured to movably support a couchtop on which an examined subject (hereinafter, "patient") P is placed. The couch 13 is configured to move the couchtop according to control exercised through the gantry 11 and a console or the like. In the bore of the gantry 11, the movable screen apparatus 15 is movably provided. To the front or the rear of the gantry 11, the projector 100 is installed. On the movable screen apparatus 15, a picture from the projector 100 is projected.

The projector controlling apparatus 200 is a computer apparatus configured to control the projector 100. The projector controlling apparatus 200 is configured to supply the projector 100 with data related to the picture to be projected. The projector 100 is configured to project the picture corresponding to the data received from the projector controlling apparatus 200, onto a screen of the movable screen apparatus 15. The projector 100 has installed therein at least a display machine and a light source. The display machine is configured to display the picture corresponding to the data received from the projector controlling apparatus 200. The light source is configured to radiate light onto the display machine either directly or indirectly via an optical system. Light (hereinafter, "projection light") that has passed through or has been reflected by the display machine is emitted to the outside of the projector 100 either directly or indirectly via an optical system. As a result of the projection light being radiated onto the movable screen apparatus 15, the picture corresponding to the projection light is projected on the movable screen apparatus 15.

The imaging controlling unit 17 functions as a core of the medical image diagnosis apparatus 10. For example, the imaging controlling unit 17 is configured to control the gantry 11 for performing a medical imaging process. Further, the imaging controlling unit 17 is configured to reconstruct a medical image related to the patient P, on the basis of raw data acquired by the gantry 11 in the medical imaging process. In this situation, the imaging controlling unit 17 may be configured to be able to control the projector 100 via the projector controlling apparatus 200. Further, possible configurations of the medical image diagnosis system 1 in the present embodiment are not limited to the configuration described above.

By employing the projector 100 and the movable screen apparatus 15, the medical image diagnosis system 1 according to the present embodiment makes it possible to enhance habitability in the bore during medical imaging processes performed by the medical image diagnosis apparatus 10. The medical image diagnosis apparatus 10 according to the present embodiment may be any apparatus capable of imaging the patient P by using the gantry 11 that has formed the bore therein. More specifically, the medical image diagnosis apparatus 10 according to the present embodiment is applicable to a single modality such as an Magnetic Resonance Imaging (MRI) apparatus, an X-ray Computed Tomography (CT) apparatus, a Positron Emission Tomography (PET) apparatus, or a Single Photon Emission Computed Tomography (SPECT) apparatus. Alternatively, the medical image diagnosis apparatus 10 may be applied to a composite modality such as an MR/PET apparatus, a CT/PET apparatus, an MR/SPECT apparatus, or a CT/SPECT apparatus. However, to explain specific examples below, the medical image diagnosis apparatus 10 according to the present embodiment will be assumed to be a magnetic resonance imaging apparatus 10. Further, the medical image diagnosis system 1 including the magnetic resonance imaging apparatus 10, the projector 100, and the projector controlling apparatus 200 will be referred to as a magnetic resonance imaging system 1.

Figure 2:
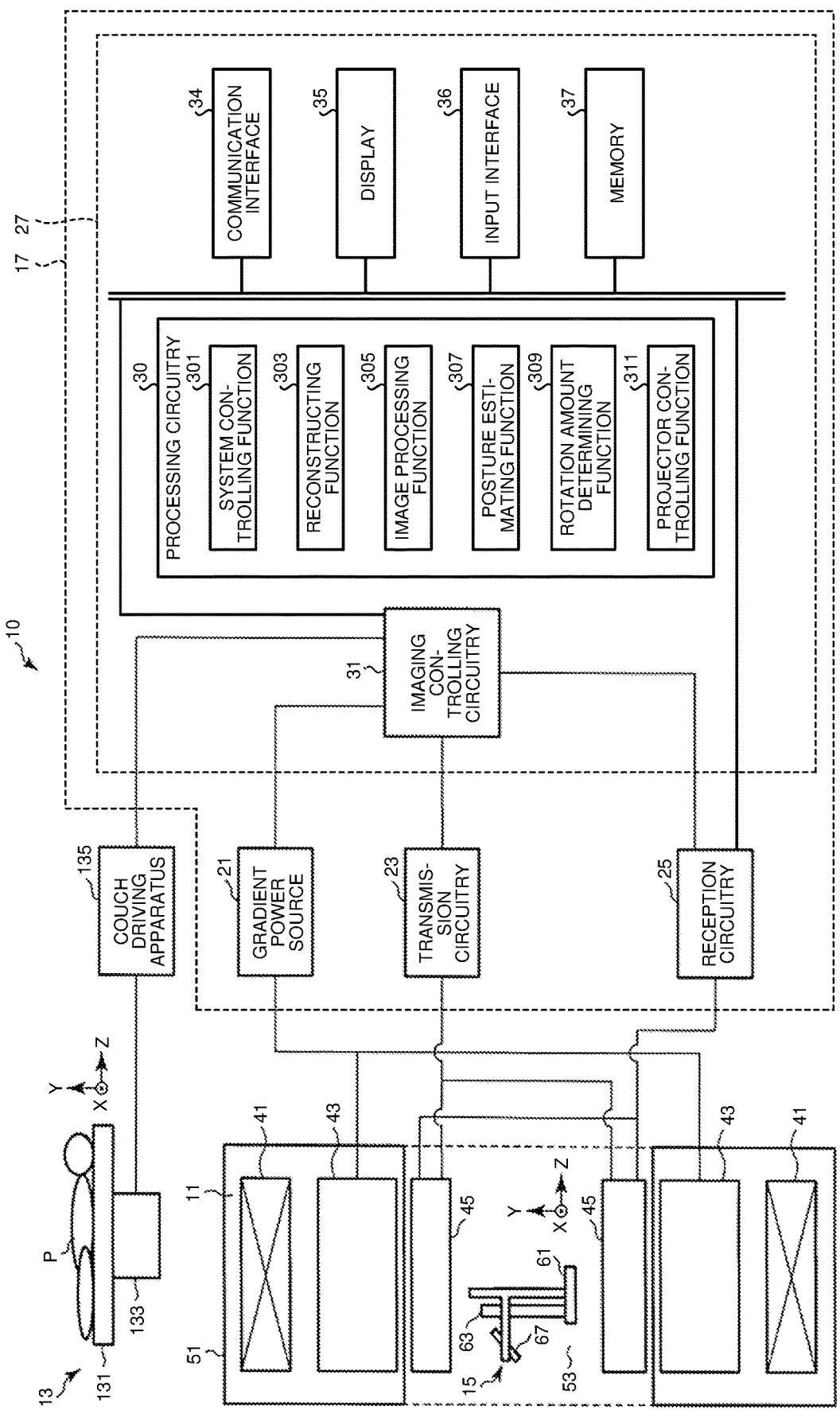
FIG. 2 is a diagram illustrating an exemplary configuration of a magnetic resonance imaging apparatus according to the embodiment.

FIG. 2 is a diagram illustrating a configuration of the magnetic resonance imaging apparatus 10 according to the present embodiment. As illustrated in FIG. 2, the magnetic resonance imaging apparatus 10 includes the imaging controlling unit 17, the gantry 11, the couch 13, and the movable screen apparatus 15. The imaging controlling unit 17 includes a gradient power source 21, transmission circuitry 23, reception circuitry 25, and a console 27. The console 27 includes imaging controlling circuitry 31, processing circuitry 30, a communication interface 34, a display 35, an input interface 36, and a memory 37. The imaging controlling circuitry 31, the processing circuitry 30, the communication interface 34, the display 35, the input interface 36, and the memory 37 are communicably connected to one another via a bus. The gradient power source 21, the transmission circuitry 23, and the reception circuitry 25 are provided separately from the console 27 and the gantry 11.

The gantry 11 includes a static magnetic field magnet 41, a gradient coil 43, and a Radio Frequency (RF) coil 45. Further, the static magnetic field magnet 41 and the gradient coil 43 are housed in a casing (hereinafter, "gantry casing") 51 of the gantry 11. In a bore 53 of the gantry casing 51, the RF coil 45 is disposed. Further, in the bore 53 of the gantry casing 51, the movable screen apparatus 15 according to the present embodiment is disposed.

The static magnetic field magnet 41, the gradient coil 43, the RF coil 45, and the like correspond to a medical imaging mechanism. Further, when the medical image diagnosis apparatus 10 is one of various types of modalities such as a CT apparatus, a PET apparatus, a SPECT apparatus, a CT/PET apparatus, an MR/PET apparatus, an MR/SPECT apparatus, or a CT/SPECT apparatus, the medical imaging mechanism corresponds to a set of various types of imaging machines provided for the gantry of any of these modalities.

The static magnetic field magnet 41 has a hollow substantially circular cylindrical shape and is configured to generate a static magnetic field on the inside of the substantially circular cylinder. For example, as the static magnetic field magnet 41, it is possible to use a permanent magnet, a superconductive magnet, or a resistive magnet. In this situation, while the central axis of the static magnetic field magnet 41 is defined as a Z-axis, an axis vertically orthogonal to the Z-axis will be referred to as a Y-axis, whereas an axis horizontally orthogonal to the Z-axis will be referred as an X-axis. The X-axis, the Y-axis, and the Z-axis structure an orthogonal three-dimensional coordinate system.

The gradient coil 43 is a coil unit attached to the inside of the static magnetic field magnet 41 and formed to have a hollow substantially circular cylindrical shape. The gradient coil 43 is configured to generate a gradient magnetic field by receiving a supply of an electric current from the gradient power source 21.

The gradient power source 21 is configured to supply the electric current to the gradient coil 43 according to control exercised by the imaging controlling circuitry 31. The gradient power source 21 is configured to cause the gradient coil 43 to generate the gradient magnetic field, by supplying the electric current to the gradient coil 43.

The RF coil 45 is arranged on the inside of the gradient coil 43 and is configured to generate a radio frequency magnetic field by receiving a supply of an RF pulse from the transmission circuitry 23. Further, the RF coil 45 is configured to receive a magnetic resonance signal (hereinafter, "MR signal") occurring from targeted atomic nuclei present in the patient P due to an action of the radio frequency magnetic field. The received MR signal is supplied to the reception circuitry 25 in a wired or wireless manner. Further, although the RF coil 45 is described above as a coil having transmitting and receiving functions, it is also acceptable to provide a transmission RF coil and a reception RF coil separately.

Via the RF coil 45, the transmission circuitry 23 is configured to transmit, to the patient P, the radio frequency magnetic field for exciting the targeted atomic nuclei such as protons, for example, that are present in the patient P. More specifically, the transmission circuitry 23 is configured to supply the RF coil 45 with a radio frequency signal (an RF signal) for exciting the targeted atomic nuclei, according to control exercised by the imaging controlling circuitry 31. The radio frequency magnetic field generated by the RF coil 45 vibrates at a resonance frequency unique to the targeted atomic nuclei and excites the targeted atomic nuclei. The MR signal occurs from the excited targeted atomic nuclei and is detected by the RF coil 45. The detected MR signal is supplied to the reception circuitry 25.

The reception circuitry 25 is configured to receive the MR signal occurring from the excited targeted atomic nuclei via the RF coil 45. The reception circuitry 25 is configured to generate a digital MR signal (hereinafter, "MR data") by performing signal processing on the received MR signal. The MR data is output to the processing circuitry 30 via the imaging controlling circuitry 31.

The couch 13 is installed adjacent to the gantry 11. The couch 13 includes a couchtop 131 and a pedestal 133. On the couchtop 131, the patient P is placed. The pedestal 133 is configured to slidably support the couchtop 131 along the X-axis, the Y-axis, and the Z-axis. The pedestal 133 houses therein a couch driving apparatus 135. The couch driving apparatus 135 is configured to move the couchtop 131 under control of the imaging controlling circuitry 31. For example, it is acceptable to use any motor such as a servo motor or a stepping motor, as the couch driving apparatus 135. With this configuration, the couchtop 131 is configured to be insertable into the bore 53.

The imaging controlling circuitry 31 is configured to perform an imaging process on the patient P, by controlling the gradient power source 21, the transmission circuitry 23, the reception circuitry 25, and the like, according to an image taking protocol output from the processing circuitry 30. The image taking protocol includes a pulse sequence corresponding to the type of a medical examination. The image taking protocol is defined with a magnitude of the electric current to be supplied by the gradient power source 21 to the gradient coil 43; timing with which the electric current is to be supplied by the gradient power source 21 to the gradient coil 43; a magnitude and a time width of the radio frequency pulse to be supplied by the transmission circuitry 23 to the RF coil 45; timing with which the radio frequency pulse is to be supplied by the transmission circuitry 23 to the RF coil 45; timing with which the MR signal is to be received by the RF coil 45; and the like. On the basis of the pulse sequence supplied from a system controlling function 301, the imaging controlling circuitry 31 is configured to control the gradient power source 21, the transmission circuitry 23, and the reception circuitry 25 in a synchronized manner, so as to image the patient P by using the pulse sequence corresponding to pulse sequence information.

Upon receipt of the MR data from the reception circuitry 25 as a result of imaging the patient P by driving the gradient power source 21, the transmission circuitry 23, and the reception circuitry 25, and the like, the imaging controlling circuitry 31 is configured to transfer the received MR data to the processing circuitry 30 or the like.

The imaging controlling circuitry 31 is realized by using a processor, for example. The term "processor" denotes, for example, a Central Processing Unit (CPU), a Graphics Processing Unit (GPU), or circuitry such as an Application Specific Integrated Circuit (ASIC) or a programmable logic device (e.g., a Simple Programmable Logic Device (SPLD), a Complex Programmable Logic Device (CPLD), or a Field Programmable Gate Array (FPGA)).

When the processor is a CPU, for example, the processor is configured to realize the functions by reading and executing the programs saved in the memory 37. In another example, when the processor is an ASIC, instead of having the programs saved in the memory 37, the functions are directly incorporated in the circuitry of the processor as logic circuitry. The processors in the present embodiment do not each necessarily have to be structured as a single piece of circuitry. It is also acceptable to structure one processor, by combining together a plurality of pieces of independent circuitry, so as to realize the functions thereof. Further, although the example was explained in which the single piece of storage circuitry is configured to store therein the programs corresponding to the processing functions, it is also acceptable to provide a plurality of pieces of storage circuitry in a distributed manner, so that the processing circuitry reads a corresponding program from each of the individual pieces of storage circuitry.

The communication interface 34 is configured to perform data communication with the projector controlling apparatus 200 or with the projector 100, in wired or wireless manner (not illustrated). Further, the communication interface 34 may also perform data communication with an external apparatus, such as a server of a medical image management system (e.g., a Picture Archiving and Communication System (PACS)) or a server of a Hospital Information System (HIS), that is connected via a network or the like (not illustrated). Furthermore, the communication interface 34 may also perform data communication with a machine (explained later) attached to the movable screen apparatus 15.

The display 35 is configured to display various types of information. For example, the display 35 is configured to display an MR image reconstructed by a reconstructing function 303 and an MR image on which an image processing process has been performed by an image processing function 305. Further, the display 35 may also display the picture projected by the projector 100.

The input interface 36 is configured to receive various types of commands from a user. As the input interface 36, it is possible to use a keyboard, a mouse, various types of switches, and/or the like. The input interface 36 is configured to supply an input signal that is input according to a user instruction, to the processing circuitry 30 via the bus. In this situation, the input interface 36 does not necessarily have to include one or more physical operational component parts such as a mouse, a keyboard, and/or the like. Examples of the input interface 36 include, for instance, electrical signal processing circuitry configured to receive an electrical signal corresponding to an input operation from an external input machine provided separately from the magnetic resonance imaging apparatus 10 and to output the electrical signal to various types of circuitry.

The memory 37 is realized by using a storage apparatus configured to store therein various types of information, such as a Hard Disk Drive (HDD), a Solid State Drive (SSD), or an integrated circuit storage apparatus. Further, the memory 37 may be realized by using a Compact Disk Read-Only Memory (CD-ROM) drive, a Digital Versatile Disk (DVD) drive, a drive apparatus configured to read and write various types of information from and to a portable storage medium such as a flash memory. For example, the memory 37 is configured to store therein MR images, a control program for the magnetic resonance imaging apparatus 10, and the like.

The processing circuitry 30 is realized by using the processor explained above or the like. The processing circuitry 30 includes the system controlling function 301, the reconstructing function 303, the image processing function 305, a posture estimating function 307, a rotation amount determining function 309, a projector controlling function 311, and the like. The processing circuitry 30 realizing the system controlling function 301, the reconstructing function 303, the image processing function 305, the posture estimating function 307, the rotation amount determining function 309, and the projector controlling function 311 correspond to a system controlling unit, a reconstructing unit, an image processing unit, a posture estimating unit, a rotation amount determining unit, and a projector controlling unit, respectively. The functions such as the system controlling function 301, the reconstructing function 303, the image processing function 305, the posture estimating function 307, the rotation amount determining function 309, and the projector controlling function 311 are stored in the memory 37, in the form of computer-executable programs.

For example, the processing circuitry 30 is configured to realize the functions corresponding to the programs, by reading and executing the programs from the memory 37. In other words, the processing circuitry 30 that has read the programs has the functions such as the system controlling function 301, the reconstructing function 303, the image processing function 305, the posture estimating function 307, the rotation amount determining function 309, and the projector controlling function 311.

By employing the system controlling function 301, the processing circuitry 30 is configured to control the entirety of the magnetic resonance imaging apparatus 10. More specifically, the system controlling function 301 is configured to read the control program stored in the memory 37, to load the read control program into a memory, and to control functional units of the magnetic resonance imaging apparatus 10 according to the loaded control program. For example, the system controlling function 301 is configured to read the image taking protocol from the memory 37, on the basis of an image taking condition input by an operator via the input interface 36. The system controlling function 301 is configured to transmit the image taking protocol to the imaging controlling circuitry 31 so as to control the imaging process performed on the patient P.

By employing the reconstructing function 303, the processing circuitry 30 is configured to reconstruct the MR image related to the patient P, on the basis of the MR data received from the reception circuitry 25. For example, the reconstructing function 303 is configured to generate the MR image defined in real space, by performing a Fourier transform or the like on the MR data arranged in either a k-space of a frequency space.

By employing the image processing function 305, the processing circuitry 30 is configured to perform various types of image processing processes on the reconstructed MR image. In this situation, the image processing function 305 may be realized by using an ASIC, an FPGA, a CPLD, or an SPLD. Details of processes performed by the posture estimating function 307, the rotation amount determining function 309, and the projector controlling function 311 realized by the processing circuitry 30 will be explained later.

Next, the magnetic resonance imaging apparatus 10 according to the present embodiment will be explained in detail.

Figure 3:
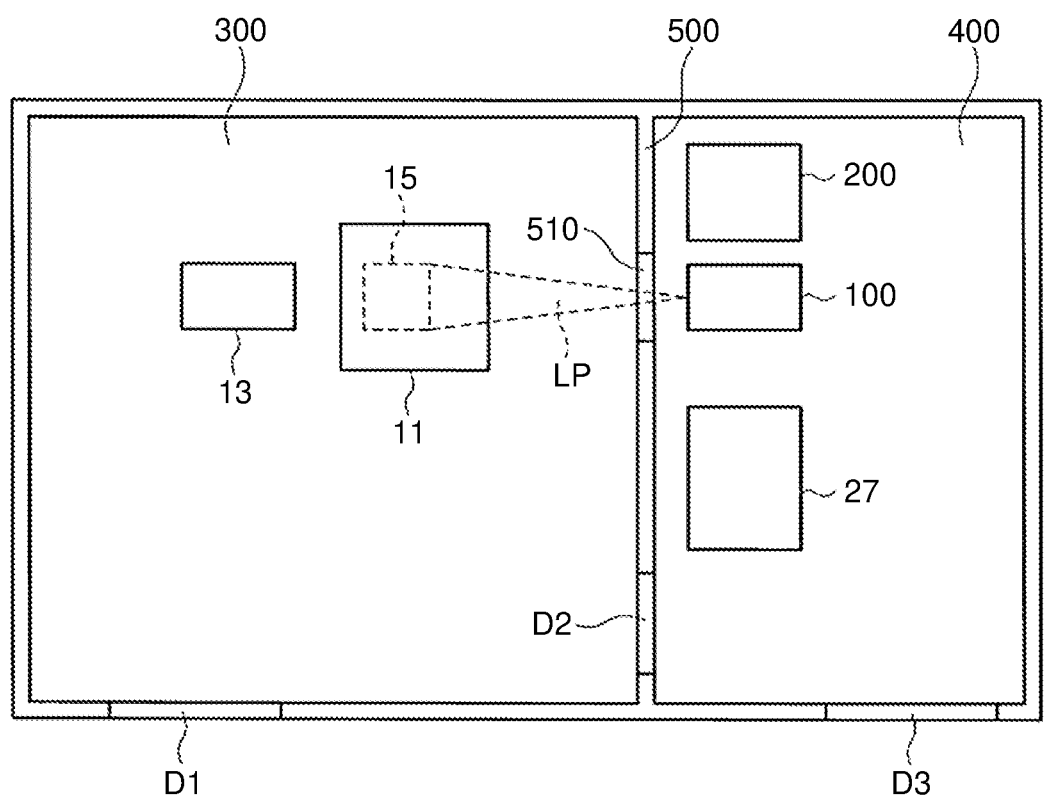
FIG. 3 is a diagram illustrating an example of an installation environment of a magnetic resonance imaging system according to the embodiment.

To begin with, an installation environment of the magnetic resonance imaging system 1 according to the present embodiment will be explained, with reference to FIG. 3. FIG. 3 is a diagram illustrating an example of the installation environment of the magnetic resonance imaging system 1 according to the present embodiment. As illustrated in FIG. 3, provided in the installation environment of the magnetic resonance imaging system 1 are an examination room 300 where an MR imaging process is performed and a control room 400 positioned adjacent to the examination room 300.

In the examination room 300, the gantry 11 and the couch 13 are installed. The couch 13 is provided to the front of the gantry 11. In the bore 53 of the gantry 11, the movable screen apparatus 15 is provided.

The examination room 300 is a shield room capable of blocking a leakage magnetic field from the gantry 11, electromagnetic fields from the outside, and the like. The examination room 300 is provided with a door D1 used for entering and exiting the room. Further, provided between the examination room 300 and the control room 400 is a door D2 used for coming and going between the examination room 300 and the control room 400. In the control room 400, the console 27, the projector 100, and the projector controlling apparatus 200 are installed. The projector 100 is installed to the rear of the gantry 11, while a wall 500 separating the examination room 300 from the control room 400 is interposed therebetween. Further, on the wall surface and/or the ceiling of the examination room 300, a camera capable of imaging the patient P and/or a camera capable of imaging a reflection board 67 of a movable member 61 (explained later) may be provided. The camera capable of imaging one or both of the patient P and the reflection board 67 may be provided on the inner wall of the gantry casing 51. In that situation, the camera is configured to image the inside of the bore 53. Data (hereinafter, "imaged data") output from the camera is output by the camera to the processing circuitry 30 in a wireless or wired manner.

The wall 500 has, in a part where projection light LP is propagated from the projector 100 toward the movable screen apparatus 15, a window 510 through which the projection light LP can be transmitted. Via the window 510, the projection light LP is propagated from the projector 100 installed in the control room 400, onto the movable screen apparatus 15 provided in the examination room 300. It is a good idea to also provide the control room 400 with a door D3 used for entering and exiting the room.

The layout described above is merely an example, and possible embodiments are not limited to this example. For instance, although the example was explained in which the projector 100, the projector controlling apparatus 200, and the console 27 are installed in the control room 400, the console 27 and the projector controlling apparatus 200 may be installed in another room different from the room having the projector 100. Further, when it is possible to form the projector 100 with a material that is not impacted by magnetic fields, the projector 100 may be provided in the examination room 300. In another example, in addition to the examination room 300 and the control room 400, it is also acceptable to provide a mechanical room or the like in which the gradient power source 21 and the reception circuitry 25 are installed.

In a lower part of the bore 53 of the gantry casing 51, a rail 55 extending parallel to the central axis Z of the bore 53 is provided. The rail 55 is a structure configured to guide sliding of the couchtop 131 and the movable screen apparatus 15 along the central axis Z. The rail 55 is provided on the inner wall of the gantry casing 51 that is in contact with the bore 53. The rail 55 is formed by using a non-magnetic material that does not act on the magnetic field used for magnetic resonance imaging processes. In this situation, with regard to the Z-axis, the direction from the couch toward the projector is defined as a +Z axis direction, whereas the direction from the projector toward the couch is defined as a −Z axis direction.

Figure 4:
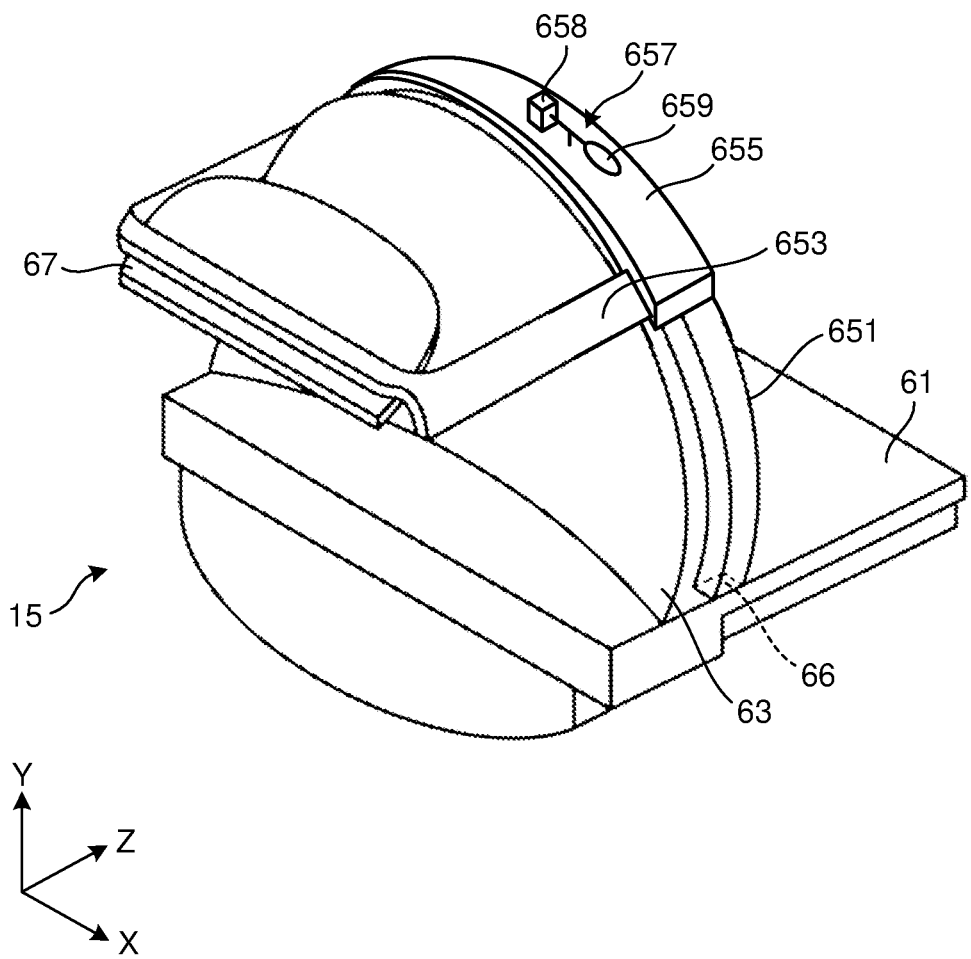
FIG. 4 is a perspective view of a movable screen apparatus according to the embodiment.
Figure 5:
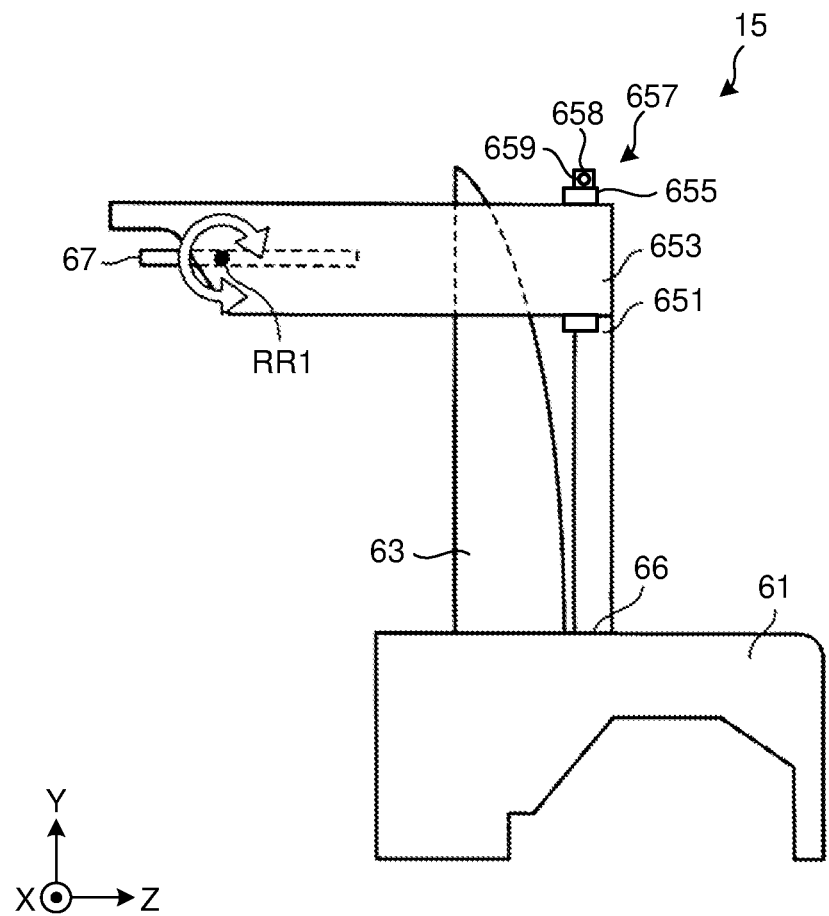
FIG. 5 is a side view of the movable screen apparatus in FIG. 4.
Figure 6:
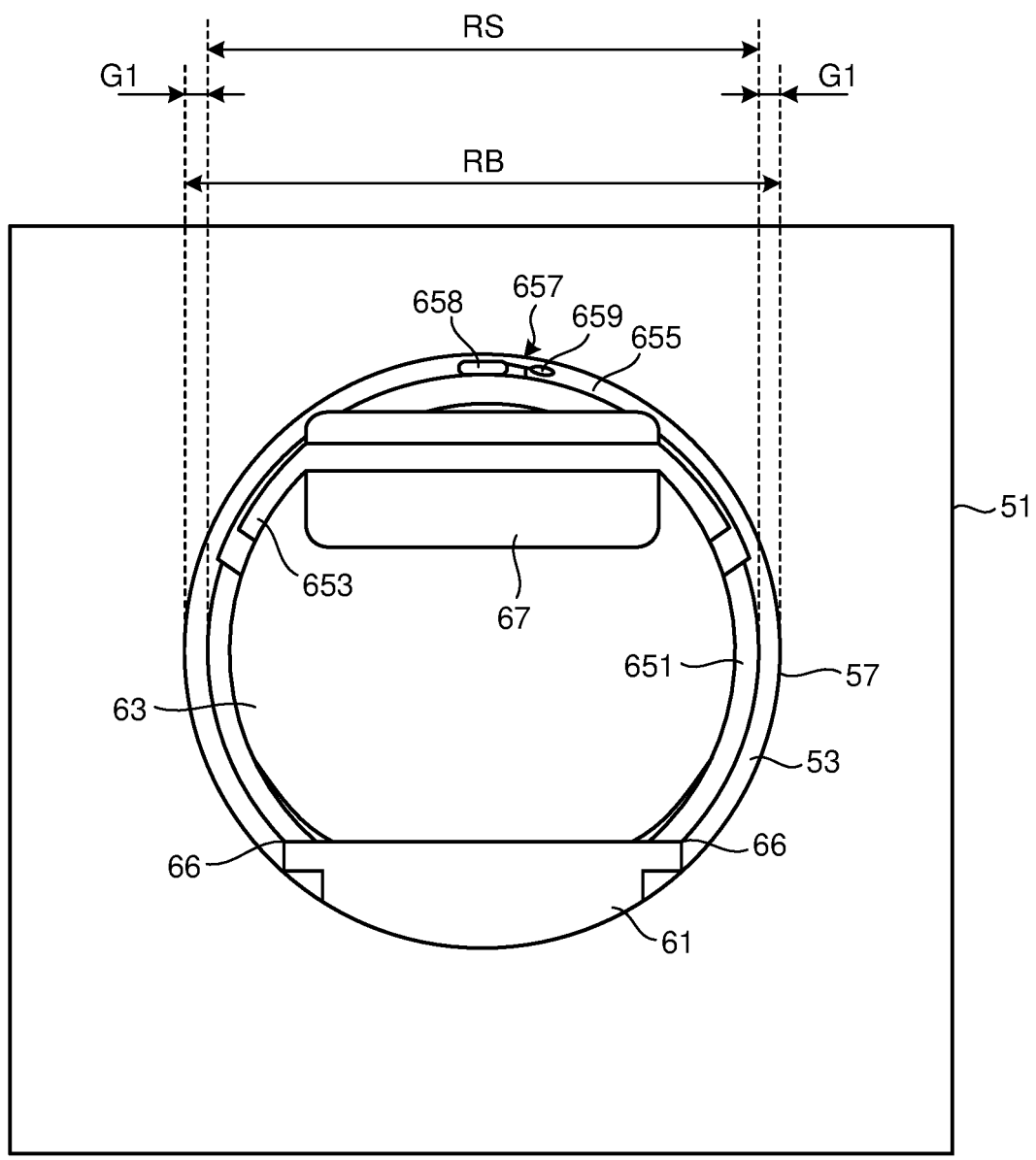
FIG. 6 is a front view of the movable screen apparatus in FIG. 4.
Figure 7:
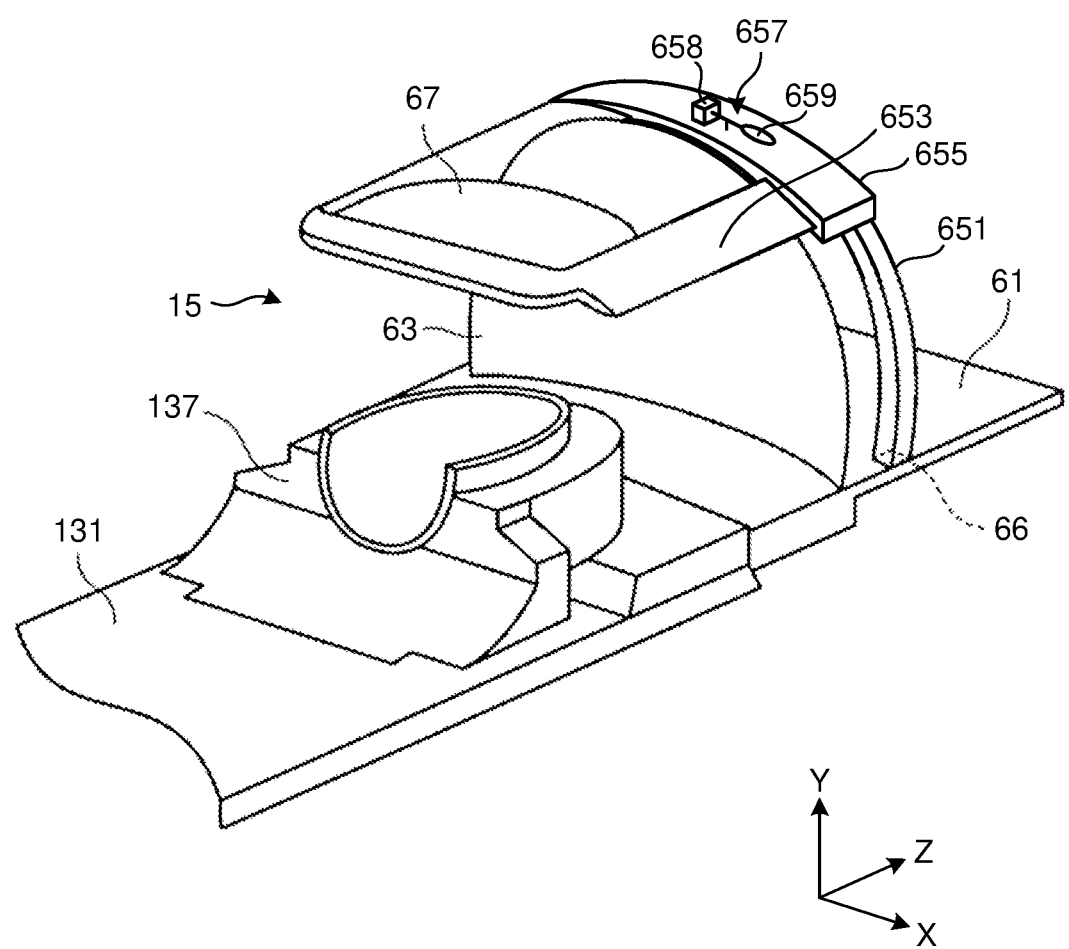
FIG. 7 is a perspective view according to the embodiment illustrating the movable screen apparatus and a couchtop that are joined together.

Next, a structure of the movable screen apparatus 15 will be explained, with reference to FIGS. 4 to 7. FIG. 4 is a perspective view of the movable screen apparatus 15 according to the present embodiment. FIG. 5 is a side view of the movable screen apparatus 15. FIG. 6 is a front view of the movable screen apparatus 15. FIG. 7 is a perspective view of the movable screen apparatus 15 and the couchtop 131 positioned adjacent to each other.

As illustrated in FIGS. 4 to 7, the movable screen apparatus 15 includes the movable member 61, a screen 63, a first frame 651, a second frame 653, and the reflection board 67. The movable member 61 is a structure (a movable wheeled base) configured to move along the rail 55 provided on an inner wall 57 of the gantry casing 51. In a lower part of the movable member 61, one or more wheels (not illustrated) that roll on the rail 55 are attached so as to enhance slidability on the rail 55. However, as long as the movable member 61 is able to move along the rail 55, the wheels do not necessarily have to be provided. It is sufficient when the surface that is in contact with the rail 55 is formed with a material having a small friction coefficient. Alternatively, it is also acceptable to provide a guiding member such as a linear motion bearing, in place of the rail 55 and the wheels. With any of these arrangements, the movable member 61 is movable in the bore 53 along the central axis Z of the bore 53, the bore 53 being formed in the gantry 11 provided with the medical imaging mechanism related to imaging the patient P. The movable member 61 is configured to support the screen 63 and the first frame 651. The movable member 61 is formed by using a non-magnetic material such as resin that does not act on magnetic fields.

As illustrated in FIG. 7, for example, the movable member 61 and the couchtop 131 may be positioned adjacent to each other. In that situation, the movable member 61 is movable in the bore along the central axis Z of the bore 53, together with the couchtop 131. In other words, the movable member 61 is movable in the bore 53, along the central axis Z of the bore 53, the bore 53 being formed in the gantry 11 provided with the medical imaging mechanism related to imaging the patient P. In a front part (the side toward the +Z axis direction) of the couchtop 131, a patient stabilization fixture 137 is attached. The patient stabilization fixture 137 is configured to stabilize the head of the patient P placed on the couchtop 131. The patient stabilization fixture 137 has a curved shape so as to be able to cover the occipital part, without blocking the field of vision of the patient P placed on the couchtop 131 in a supine posture. In other words, the patient stabilization fixture 137 is open on the side corresponding to the frontal part of the head.

In this situation, the patient stabilization fixture 137 connected to the movable member 61 does not necessarily need to be configured to stabilize the head of the patient P in a supine posture. For example, the patient stabilization fixture 137 connected to the movable member 61 may be configured to stabilize the head of the patient P placed on the couchtop 131 in a prone posture or a side lying posture. For example, when the patient stabilization fixture 137 is configured to stabilize the head of the patient placed on the couchtop 131 in a prone posture, one of the movable member 61 and the couchtop 131 is provided with a reflection board (hereinafter, "downward mirror") configured to enable the patient in the prone posture to view a picture projected on the screen 63. With this arrangement, the patient in the prone posture is able to view the picture projected on the screen 63, via the downward mirror provided for one of the movable member 61 and the couchtop 131.

As illustrated in FIGS. 4 to 7, the screen 63 is provided for the movable member 61. Onto the screen 63, the picture from the projector 100 is projected. More specifically, on the screen 63, the picture from the projector 100 is projected from the side opposite to the side where the couchtop 131 is inserted into the bore 53. In other words, the projector 100 is positioned on the opposite side from the couch 13 while the screen 63 is interposed therebetween. In this situation, the surface of the screen 63 facing the projector 100 will be referred to as the rear surface, whereas the surface facing the couch 13 will be referred to as the front surface. To display the picture on the front surface, it is a good idea to form the screen 63 by using a translucent material. Examples of the translucent material include translucent plastic and frosted glass. As a result of forming the screen 63 by using the translucent material, the projection light emitted from the projector 100 is radiated onto the rear surface of the screen 63, so that the picture corresponding to the projection light is displayed on the front surface. As a result, the patient P and the like are able to view the picture displayed on the front surface, from the couch 13 side via the reflection board 67.

The screen 63 may be of a type having a planar shape or may be of a type having a curved shape. When having a curved shape, the screen may be positioned so that the concave surface thereof faces the couch 13, i.e., serves as the front surface. When the concave surface faces the couch 13, it is possible to cover an area behind the head of the patient P placed on the couchtop 131 with the screen 63. As a result, it is possible to fill the field of view of the patient P with the picture projected on the screen 63 so that he/she is immersed in the picture.

As illustrated in FIG. 6, the first frame 651 has an outside diameter RS smaller than the diameter RB of the inner wall 57 that is in contact with the bore 53 of the gantry casing 51. By designing the outside diameter RS to be smaller than the inside diameter RB in this manner, it is possible to insert the movable screen apparatus 15 into the bore 53. In this situation, air is flowing into the bore 53 from a ventilation fan (not illustrated) provided for the gantry 11. By providing a gap G1 between the edges of the screen 63 and the inner wall 57, it is possible to prevent the screen 63 from blocking the air blown from the ventilation fan.

As illustrated in FIGS. 4, 5, and 7, two connection locations 66 between the first frame 651 and the movable member 61 are positioned on the projector side with respect to the screen 63, while the patient P placed on the couchtop 131 is in the state of being able to view the picture via the reflection board 67. Further, the connection locations 66 between the first frame 651 and the movable member 61 are provided in such positions on the movable member 61 that the picture projected onto the screen 63 from the projector 100 is not blocked.

The first frame 651 is connected to the movable member 61. The first frame 651 is provided on the movable member 61 so as to be movable along the central axis Z. In this situation, in addition to the above configuration, the first frame 651 is configured to support a second frame 653 so as to be movable in an outer shape direction along the outer shape (i.e., an outer circumferential direction along the outer circumference) of the first frame 651. The structure and the like of the second frame 653 will be explained in detail later. One or both of the first frame 651 and the second frame 653 may be structured by using a transparent material. Preferably, the first frame 651 and the second frame 653 are each structured by using a transparent material. As a result, it is possible to reduce oppressing feelings which may be caused on the patient P by the first frame 651 and the second frame 653.

As illustrated in FIGS. 4, 5, and 7, the first frame 651 is connected to the movable member 61 at the connection locations 66 and is positioned on the projector side with respect to the screen 63. In this situation, the position of the first frame 651 is arranged on the outside of the field of view of the patient P placed on the couchtop 131. The first frame 651 is shaped, for example, so as to curve along the inner wall 57 of the bore 53. However, possible shapes of the first frame 651 are not limited to arc shapes as described above, as long as the picture projected onto the screen 63 from the projector 100 is not blocked.

As illustrated in FIGS. 4 to 7, the second frame 653 is supported by the first frame 651 so as to be movable along the first frame 651 via a connection frame 655. The second frame 653 is configured to support the reflection board 67 reflecting the picture projected on the screen 63. The second frame 653 passes through the gap between the outer edge of the screen 63 and the inner wall 57 of the bore 53. In other words, the second frame 653 is configured to support the reflection board 67 while extending from the first frame 651 beyond the screen 63.

For example, the second frame 653 is configured to support the reflection board 67 while straddling the screen 63, by going through the gap between the outer edges of the screen 63 and the inner wall 57 of the bore 53. More specifically, in the gap between the inner wall 57 of the bore 53 and the screen 63, the second frame 653 is structured with two arms extending parallel to the central axis Z of the bore 53. By using the two arms, the second frame 653 is configured to rotatably support the reflection board 67 while using an axis perpendicular to the Z-axis as a rotation axis. In this situation, the cross-sectional shape of each of the two arms is a shape curved along the inner wall 57 of the bore 53. As a result, it is possible to adjust the angle of the reflection board 67 around the rotation axis, as appropriate.

In an example, the second frame 653 may be supported by the first frame 651 so as to be able to move toward the projector along the central axis Z of the bore 53. In that situation, for example, a linear motion bearing is provided between the second frame 653 and the connection frame 655. On such occasion, the second frame 653 is provided with a guiding rail that guides a block of the linear motion bearing, along the central axis Z of the bore 53. In that situation, the block is provided for the connection frame 655. The linear motion bearing is configured by using a non-magnetic material.

As illustrated in FIGS. 4 to 7, the connection frame 655 is configured to support the second frame 653 so as to be movable along the outer circumference of the first frame 651 (i.e., the outer edge of the first frame 651). As illustrated in FIGS. 4 to 7, each end of the connection frame 655 is able to move as far as to a corresponding one of the connection locations 66. Between the connection frame 655 and the first frame 651, for example, a rack and pinion mechanism may be provided. In that situation, the first frame 651 is provided with a rack gear extending along the outer circumference of the first frame 651. Further, the connection frame 655 is provided with a pinion gear that engages with the rack gear. Possible methods for realizing the connection between the first frame 651 and the connection frame 655 are not limited to the rack and pinion mechanism. It is possible to realize the connection by using other mechanisms such as a linear motion bearing, for example. In that situation, the first frame 651 is provided with a guiding rail that guides a block of the linear motion bearing in the manner of an arc. In addition, the block is provided on the connection frame 655. The rack and pinion mechanism and the linear motion bearing described above are each configured by using a non-magnetic material.

Figure 8:
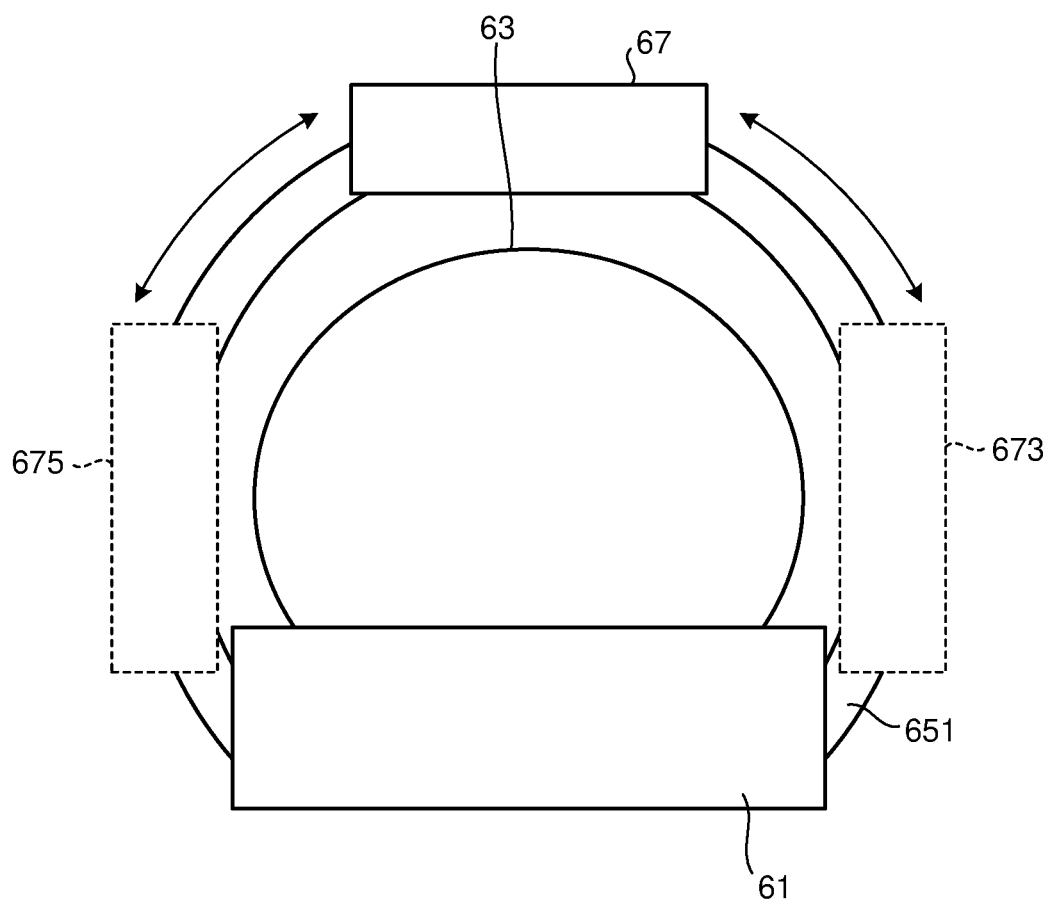
FIG. 8 is a schematic front view according to the embodiment illustrating the movable screen apparatus related to moving of a reflection board along a first frame.

FIG. 8 is a schematic front view illustrating the movable screen apparatus 15 related to moving of the reflection board 67 along the first frame 651. In FIG. 8, for the sake of convenience in the explanation, the second frame 653 and the connection frame 655 are omitted. As illustrated in FIG. 8, by moving the connection frame 655, it is possible to move the reflection board 67 from a predetermined position as far as to end positions 673 and 675 along the outer circumference of the first frame 651. The moving of the connection frame 655 is realized, for example, by a manual operation performed by the user or driving of the pinion gear or the block provided for the connection frame 655. Because it is possible to control the driving of the pinion gear or the block, by using one of various types of known motors, explanations thereof will be omitted.

The connection frame 655 is provided with a fixing mechanism 657 configured to fix the connection frame 655 onto the first frame 651. As illustrated in FIGS. 4 to 7, for example, the fixing mechanism 657 includes: a pressing member 658 configured to press against the first frame 651; and a lever 659 configured to enable the user to operate a knob thereof. Provided in a contact part between the pressing member 658 and the first frame 651 is, for example, an elastic member (e.g., rubber) capable of fixing the connection frame 655 onto the first frame 651 with a friction force, while the pressing member 658 is pressing against the first frame 651. In this situation, the pressing member 658 may be configured to be able to fit into a plurality of holes provided in the first frame 651. On such occasion, it is not necessary to provide the elastic member. The fixing mechanism 657 is configured by using a non-magnetic material.

Figure 9:
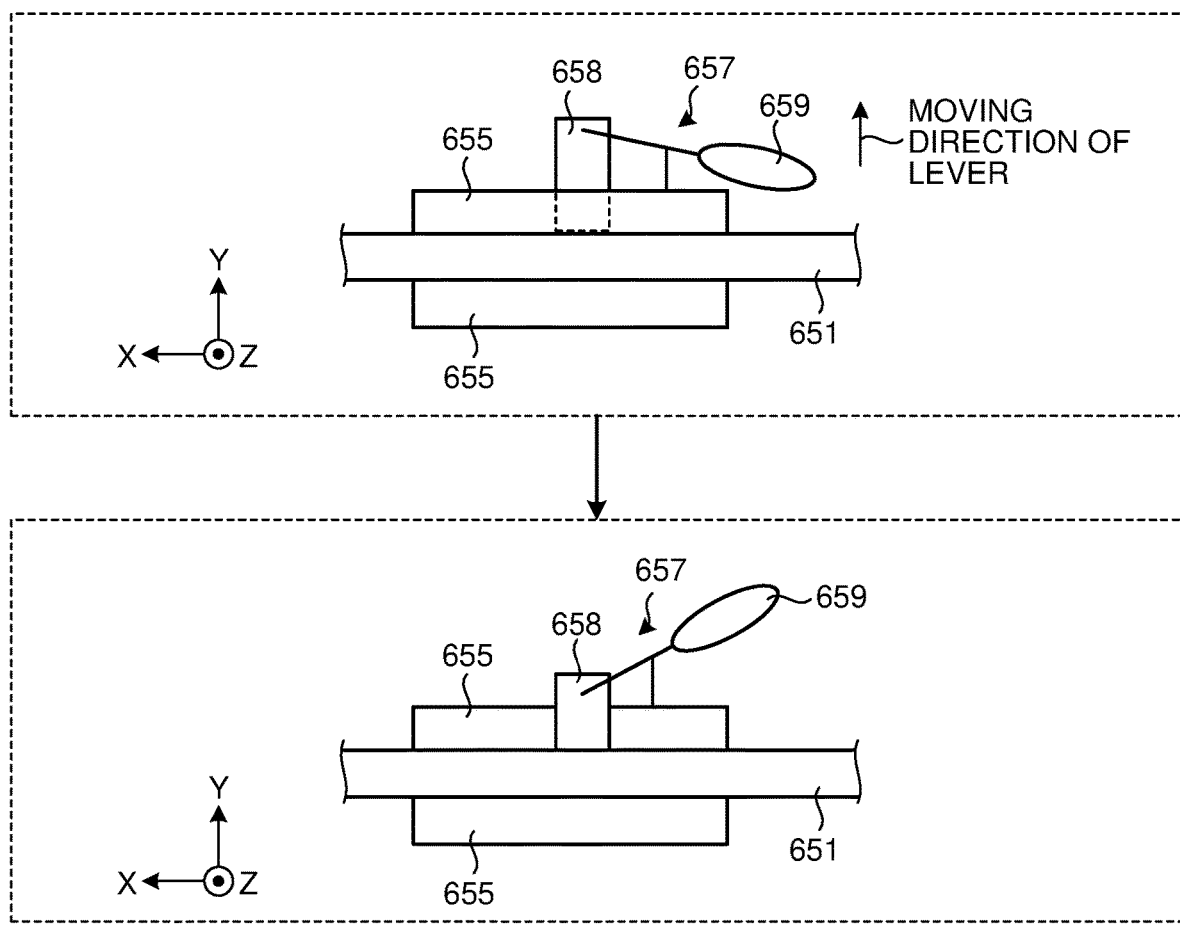
FIG. 9 presents diagrams according to the embodiment illustrating an example of a fixing operation performed by a fixing mechanism.

FIG. 9 presents diagrams illustrating an example of the fixing operation performed by the fixing mechanism 657. As illustrated in FIG. 9, when the lever 659 is moved in the direction to move away from the first frame 651, the pressing member 658 is pressed against the first frame 651. Accordingly, the connection frame 655 is fixed onto the first frame 651. The means for fixing the connection frame 655 onto the first frame 651 as presented in FIG. 9 and the above explanation is merely an example. It is possible to use other configurations as appropriate.

While the movable member 61 and the couchtop 131 are joined together, for example, the reflection board 67 is supported by the second frame 653 while being positioned apart from the surface of the movable member 61, so as not to collide with the head of the patient P placed on the couchtop 131. As illustrated in FIGS. 4 to 8, the reflection board 67 is provided at a substantially end part of the second frame 653. The reflection board 67 is configured to reflect the picture displayed on the front surface of the screen 63. The reflection board 67 is formed by using a non-magnetic material, and it is possible to use any material as long as it is possible to optically reflect a subject of reflection. For example, as the reflection board 67, a mirror obtained by applying aluminum vapor deposition on acryl or a half mirror coated with a dielectric film may be used. The patient P whose head is arranged on the patient stabilization fixture 137 is able to view the picture projected on the front surface, via the reflection board 67.

The reflection board 67 is rotatably provided on the second frame 653 so that the angle of the reflection board 67 can manually be adjusted. More specifically, as illustrated in FIG. 5, the reflection board 67 is provided on the second frame 653 so as to be rotatable on a rotation shaft RR1 by a rotating mechanism (not illustrated) provided for the second frame 653. The rotation shaft RR1 is provided on the second frame 653 so that, for example, it is possible to adjust the orientation of the reflection board 67 with respect to the front surface of the screen 63. More specifically, it is a good idea to configure the second frame 653 so as to be able to switch, at least, between a first angle for a first projection style (explained later) and a second angle for a second projection style. The first projection style is a style in which the patient P views the picture on the screen 63 from the outside of the gantry 11, without the intermediation of the reflection board 67. Accordingly, in the first projection style, the first angle of the reflection board 67 may be set to such an angle that the field of vision of the patient P or the like who is outside the gantry 11 is not blocked, e.g., to be parallel to the second frame 653. In that situation, the second frame 653 is moved toward the projector along the central axis Z or is moved as far as to the connection locations 66 along the first frame 651.

The second projection style is a style in which the patient P views the picture via the reflection board 67 while in the bore 53. When the first projection style is switched to the second projection style, the second frame 653 is moved so that the reflection board 67 is positioned directly above the patient stabilizing fixture 137, for example, when the patient P is in a supine posture as illustrated in FIGS. 4 to 7. When the patient P is not in the supine posture (e.g., is in a side lying posture), the reflection board 67 is moved to the front of the patient P either manually or automatically. As yet another example, when the patient P is in a prone posture, because the downward mirror provided for the movable member 61 or the couchtop 131 is positioned in front of the patient P, the reflection board 67 does not move. In this situation, the second angle of the reflection board 67 or the downward mirror in the second projection style may be set to an arbitrary angle between the horizontal position and the perpendicular position, in accordance with the physique or the like of the patient P who is the viewer. Further, the reflection board 67 may be configured by using a prism mirror. Furthermore, the reflection board 67 may have a Fresnel structure.

Figure 10:
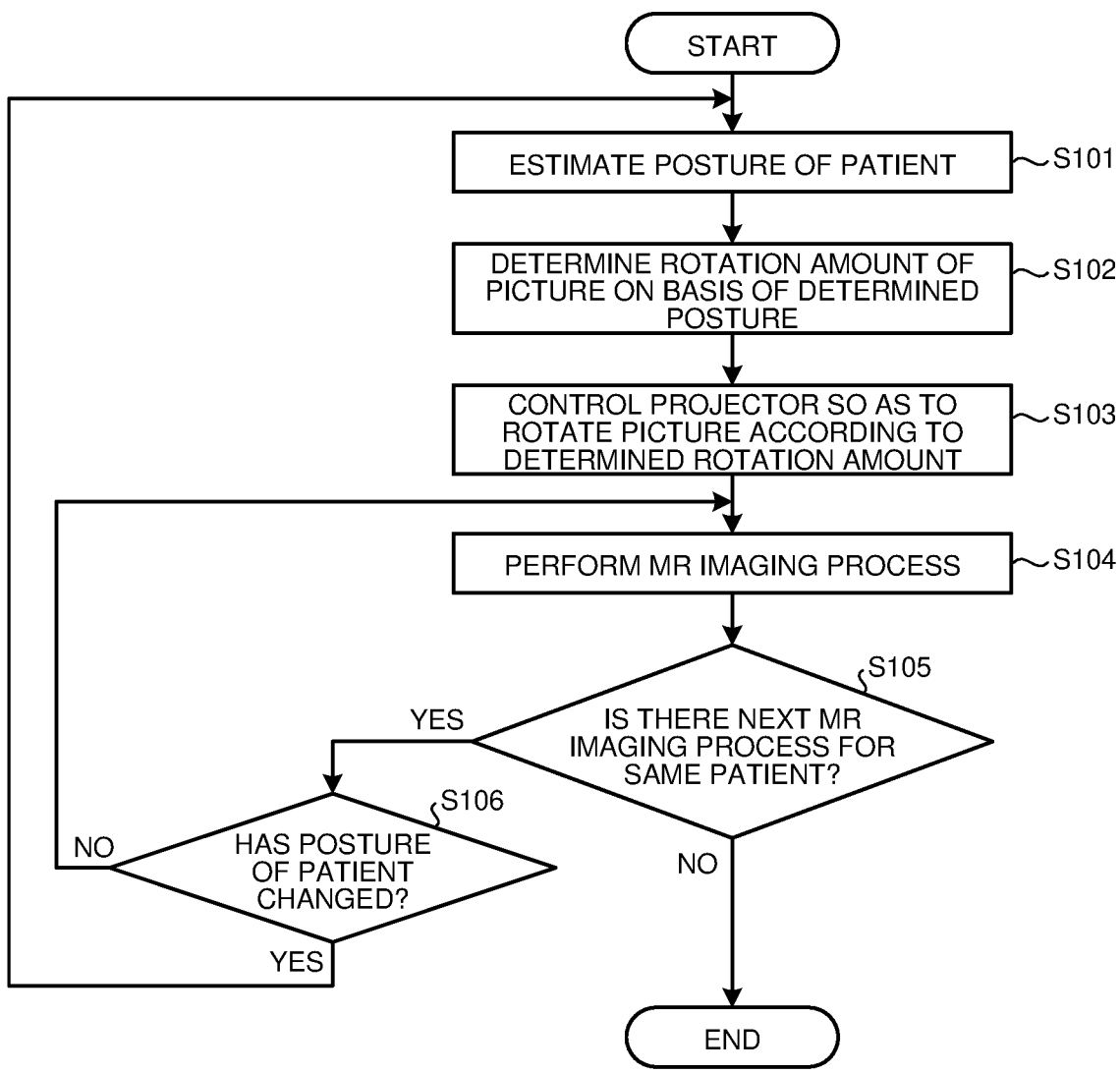
FIG. 10 is a flowchart according to the embodiment illustrating an example of a processing procedure in a picture rotating process.

Next, a process (hereinafter, "picture rotating process") to rotate the picture in accordance with postures (or body stances) of the patient P will be explained, with reference to FIG. 10. FIG. 10 is a flowchart illustrating an example of a processing procedure in the picture rotating process.

Picture Rotating Process
Step S101:

By employing the posture estimating function 307, the processing circuitry 30 estimates the posture of the patient P, on the basis of the position of the reflection board 67 with respect to the screen 63 or the orientation of the head of the patient P. More specifically, in the examination room 300, when a camera is installed on at least one selected from among a wall surface intersecting the central axis (the Z-axis) of the static magnetic field magnet 41, the ceiling of the examination room 300, and the inner wall 57 of the gantry casing 51, the posture estimating function 307 estimates the posture of the patient P, by using imaged data output from the camera capable of imaging one or both of the reflection board 67 and the patient P. For example, when the camera is a patient camera configured to image the patient P (and/or a ceiling camera), the posture estimating function 307 estimates the posture of the patient P, by identifying the orientation of the head of the patient P while using the imaged data output from the patient camera.

More specifically, by employing the posture estimating function 307, the processing circuitry 30 estimates the posture of the patient P, by performing an image recognition process on the imaged data. Even more specifically, the posture estimating function 307 estimates the posture of the patient P, by identifying a positional relationship between the orientation of the head of the patient P and the screen 63 in the image data and the orientation of the head of the patient P with respect to the reflection board 67 in a predetermined position, by performing any of various types of segmentation processes or the like. Examples of the postures of the patient P include a supine posture, side lying postures, and a prone posture. The above description corresponds to detecting the body stance of the patient P, by imaging the patient P with the use of the camera. Further, for example, after the posture of the patient P is estimated, the reflection board 67 moves to the front of the patient P.

In the above description, the picture of the patient P is requisite in the imaged data; however, possible methods for estimating the posture of the patient P are not limited the example described above. For instance, when only a part of the patient P is rendered in the imaged data or when the camera is a camera configured to image the reflection board 67 (and/or a ceiling camera), the processing circuitry 30 identifies, in the imaged data, the position of the reflection board 67 with respect to the screen 63, by performing any of various types of segmentation process, while employing the posture estimating function 307. Subsequently, the posture estimating function 307 estimates the posture of the patient P, while regarding the identified position of the reflection board 67 as the front (the frontal plane of the head) of the patient P. For example, after the reflection board 67 is moved from a predetermined position to the front of the patient P, when the position of the reflection board 67 is positioned in a 90-degree direction from the placement surface of the couchtop 131, the posture estimating function 307 determines the posture of the patient P to be a side lying posture.

In this situation, the estimation of the posture of the patient P does not necessarily have to be based on the imaged data obtained by the camera. For instance, when a tilt sensor is provided on one selected from among the reflection board 67, the second frame 653, and the connection frame 655, the processing circuitry 30 may be configured, by employing the posture estimating function 307, to estimate the posture of the patient P, by using tilt data output from the tilt sensor. More specifically, after the reflection board 67 is moved from a predetermined position to the front of the patient P, the posture estimating function 307 may be configured to estimate the posture of the patient P, by using the tilt data output from the tilt sensor to the processing circuitry 30 in a wireless or wired manner. For example, when the tilt information indicates 90°, the posture estimating function 307 estimates the posture of the patient P as a side lying posture.

Further, possible processes for estimating the posture of the patient P are not limited to the example described above. For instance, by employing the posture estimating function 307, the processing circuitry 30 may be configured to estimate the posture of the patient P, by identifying the orientation of the head of the patient P, while using an image taking condition (e.g., the image taking protocol and/or a sequence) set for the patient P. In an example, the posture estimating function 307 may estimate the posture of the patient P, by further using the purpose of the medical examination indicated in the examination order for the patient P output from a Radiology Information System (RIS) output via the communication interface 34. In that situation, the patient P is placed on the couchtop 131 in a posture corresponding to the image taking condition, i.e., the estimated posture. After that, the reflection board 67 is moved to the front of the patient P.

For example, when the image taking condition related to the patient P is input via the input interface 36, the posture estimating function 307 estimates a posture of the patient P corresponding to the input image taking condition, by using a correspondence table in which image taking conditions and postures of the patient P are kept in association with one another. Alternatively, when the image taking condition is input, if a posture (e.g., a prone posture, a supine posture, or a side lying posture) of the patient P is input as the posture of the patient P during the imaging process, the posture estimating function 307 may estimate the posture of the patient P in accordance with the input, without using the correspondence table.

Step S102:

By employing the rotation amount determining function 309, the processing circuitry 30 determines a rotation amount of the picture to be projected on the screen 63, on the basis of the posture of the patient P estimated at step S101. As a reference for the rotation amount, the angle formed when the vertical direction of the picture is equal to the Y-axis may be set to 0°. For example, when the posture of the patient P is a prone posture, the rotation amount determining function 309 determines the rotation amount to be 180°. In that situation, the picture projected on the screen 63 is an image inverted upside down. As another example, when the posture of the patient P is a side lying posture facing to the right in the positive direction on the X-axis, the rotation amount determining function 309 determines the rotation amount to be 270°. In that situation, the picture projected on the screen 63 is an image tilted toward the right by 90°.

Step S103:

By employing the projector controlling function 311, the processing circuitry 30 controls the projector 100 so as to rotate the picture to be projected on the screen 63 according to the determined rotation amount. For example, when the projector 100 can be rotated by a rotation driving mechanism along the rotation axis, the projector controlling function 311 controls the rotation driving mechanism according to the determined rotation amount. As another example, when the projector 100 has an application program configured to rotate pictures, the projector controlling function 311 executes the application program so as to rotate the picture according to the determined rotation amount. With any of these arrangements, the picture projected on the screen 63 is rotated on the rotation axis by the determined rotation amount.

Step S104:

The imaging controlling circuitry 31 executes the image taking protocol related to the patient P. Accordingly, the MR imaging process is performed for the patient P. Subsequently, by employing the reconstructing function 303, the processing circuitry 30 reconstructs the MR image related to the patient P, on the basis of the MR data output from the reception circuitry 25. By employing the system controlling function 301, the processing circuitry 30 stores the reconstructed MR image into the memory 37.

Step S105:

When there is a next MR imaging process to be performed for the same patient (step S105: Yes), the process at step S106 is performed. On the contrary, when there is no next MR imaging process for the same patient (step S105: No), the picture rotating process ends.

Step S106:

In relation to the next MR imaging process, when the posture of the patient P has changed (step S106: Yes), the process at step S101 is performed. In relation to the next MR imaging process, when the posture of the patient P has not changed (step S106: No), the process at step S104 is performed. The judgment at the present step is made by the posture estimating function 307 on the basis of, for example, a change in the relative positional relationship between the patient P and the reflection board 67 captured by the camera. Alternatively, it is also acceptable to omit the present step, so as to perform the processes at step S101 and thereafter following step S105.

In a modification example of the present embodiment, the processing circuitry 30 may estimate, by employing the posture estimating function 307, a positional relationship of the front of the patient P with the screen 63, on the basis of imaged data output from the camera, the tilt data output from the tilt sensor, or the image taking condition related to the patient P. In that situation, the rotation amount determining function 309 determines a rotation amount on the basis of the positional relationship of the front of the patient P with the screen 63.

The medical image diagnosis apparatus 10 according to the embodiment described above is configured: to estimate the posture of the patient P, on the basis of the position of the reflection board 67 with respect to the screen 63 or the orientation of the head of the patient P; to determine the rotation amount of the picture to be projected on the screen 63 on the basis of the estimated posture; and to control the projector 100 so as to rotate the picture to be projected on the screen 63 according to the determined rotation amount. For example, the medical image diagnosis apparatus 10 according to the embodiment is configured to estimate the posture of the patient P, by using the imaged data output from the camera capable of imaging one or both of the reflection board 67 and the patient P. In another example, the medical image diagnosis apparatus 10 may be configured to estimate the posture of the patient P, by using the tilt data output from the tilt sensor provided on one of the reflection board 67 and the second frame 653. In yet another example, the medical image diagnosis apparatus 10 may estimate the posture of the patient P, by identifying the orientation of the head of the patient P while using the image taking condition for the patient P. Further, one of the couchtop 131 and the movable member 61 of the medical image diagnosis apparatus 10 is provided with the reflection board (the downward mirror) configured to enable the patient P in a prone posture to view the picture projected on the screen 63. In other words, the medical image diagnosis apparatus 10 according to the embodiment is able to position the mirror in accordance with the position of the face of the patient P.

With these arrangements, the medical image diagnosis apparatus 10 according to the embodiment is able to cause the picture rotated in accordance with the posture of the patient P placed on the couchtop 131 to be projected onto the screen 63. In other words, by using the medical image diagnosis apparatus 10 according to the embodiment, the patient P is able to view the picture of which the vertical direction matches the head-to-toe direction of the patient P himself/herself, regardless of the posture of the patient P (i.e., regardless of the orientation of the face of the patient P). Consequently, the medical image diagnosis apparatus 10 according to the embodiment is able to reduce situations where the patient P experiences oppressed feelings from the movable screen apparatus 15 or feelings of having something attached, for example, in the second projection style during the MR imaging process. It is therefore possible to provide the patient P with a relaxing picture projected on the screen 63 in a wide-spread manner with feelings of presence. Consequently, the medical image diagnosis apparatus 10 according to the embodiment is able to reduce the oppressed feelings and the entrapped feelings inside the bore and is thus able to enhance a feeling of the patient P being immersed in the picture. In other words, the medical image diagnosis apparatus 10 in the present example is able to provide the patient P with a medical examination environment that sufficiently relaxes the patient P.

As explained above, the medical image diagnosis apparatus 10 in the present embodiment is able to reduce uneasiness of the patient P placed in the bore and to help the patient P feel the examination period to be shorter than the actual length of time. It is therefore possible to keep the patient P undisturbed while the imaging process is performed. Accordingly, by using the medical image diagnosis apparatus 10, it is possible to acquire the image in a stable manner, to enhance the quality of the image related to the patient P, and to improve a throughput of the medical examination for the patient P.

When technical concept of the embodiment is realized as a picture projection apparatus 700, the picture projection apparatus 700 includes, for example, the movable screen apparatus 15, the projector 100, and the projector controlling apparatus 200. The projector controlling apparatus 200 has various types of functions capable of executing the picture rotating process. The projector controlling apparatus 200 is realized by using a computer, for example. Processing circuitry of the computer includes, for example, the posture estimating function 307, the rotation amount determining function 309, and the projector controlling function 311. In another example, the picture projection apparatus 700 may be structured with the movable screen apparatus 15 and the projector controlling apparatus 200. In yet another example, when processing circuitry of the projector 100 has installed therein various types of functions capable of executing the picture rotating process, the picture projection apparatus 700 may be structured with the movable screen apparatus 15 and the projector 100.

For example, the picture projection apparatus 700 includes the movable member 61 movable in the bore 53 along the central axis Z of the bore 53, the bore 53 being formed in the gantry 11 provided with the medical imaging mechanism related to imaging the patient P; the screen 63 which is provided for the movable member 61 and onto which a picture is projected; the projector 100 configured to project the picture onto the screen 63; the first frame 651 connected to the movable member 61 and positioned on the projector 100 side relative to the screen 63; the second frame 653 that is configured to support the reflection board 67 and is movable along the first frame 651; the posture estimating unit configured to estimate the posture of the patient P on the basis of one of the position of the reflection board 67 with respect to the screen 63 and the orientation of the head of the patient P; the rotation amount determining unit configured to determine a rotation amount of the picture on the basis of the estimated posture; and the projection controlling unit configured to control the projector 100 so as to rotate the picture according to the determined rotation amount. Because the constituent elements of the picture projection apparatus 700 and the procedure and advantageous effects of the picture rotating process are the same as those in the embodiments, explanations thereof will be omitted.

According to at least one aspect of the embodiments described above, it is possible to reduce the oppressed feelings and the entrapped feelings in the bore.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis apparatus comprising:
   a movable member movable in a bore along a central axis of the bore, the bore being formed in a gantry provided with a medical imaging mechanism related to imaging an examined subject;
   a couchtop configured to be insertable into the bore;
   a screen which is provided for the movable member and onto which a picture from a projector is projected;
   a first frame connected to the movable member and positioned on the projector side relative to the screen;
   a second frame that is configured to support a reflection board and is movable along the first frame; and
   processing circuitry configured
      to estimate a posture of the examined subject, on a basis of one of a position of the reflection board with respect to the screen and an orientation of a head of the examined subject,
      to further determine a rotation amount of the picture on a basis of the posture,
      to control the projector so as to rotate the picture according to the rotation amount, and
      to estimate the posture, by using tilt data output from a tilt sensor provided on one of the reflection board and the second frame.

2. The medical image diagnosis apparatus according to claim 1, wherein the processing circuitry is configured to estimate the posture by using imaged data output from a camera capable of imaging one or both of the reflection board and the examined subject.

3. The medical image diagnosis apparatus according to claim 1, wherein one of the couchtop and the movable member is provided with a reflection board configured to enable the examined subject in a prone posture to view the picture projected on the screen.

4. A picture projection apparatus comprising:
   a movable member movable in a bore along a central axis of the bore, the bore being formed in a gantry provided with a medical imaging mechanism related to imaging an examined subject;
   a screen which is provided for the movable member and onto which a picture is projected;
   a projector configured to project the picture onto the screen;
   a first frame connected to the movable member and positioned on the projector side relative to the screen;
   a second frame that is configured to support a reflection board and is movable along the first frame; and
   a processing circuitry configured
      to estimate a posture of the examined subject on a basis of one of a position of the reflection board with respect to the screen and an orientation of a head of the examined subject, to further determine a rotation amount of the picture on a basis of the posture, to control the projector so as to rotate the picture according to the rotation amount, and to estimate the posture, by using tilt data output from a tilt sensor provided on one of the reflection board and the second frame.

\* \* \* \* \*